United States Patent [19]

Haas

[11] Patent Number: 4,715,371

[45] Date of Patent: Dec. 29, 1987

[54] LUNG-CONTROLLED DIAPHRAGM VALVE

[75] Inventor: Hans Haas, Lubeck, Fed. Rep. of Germany

[73] Assignee: Dragerwerk A.G., Fed. Rep. of Germany

[21] Appl. No.: 924,358

[22] Filed: Oct. 28, 1986

[30] Foreign Application Priority Data

Nov. 8, 1985 [DE] Fed. Rep. of Germany ....... 3539668

[51] Int. Cl.$^4$ ............................................ A61M 16/00

[52] U.S. Cl. ................................................ 128/204.26

[58] Field of Search ...................... 128/204.26, 204.27; 137/510, 908

[56] References Cited

U.S. PATENT DOCUMENTS 2,760,507 8/1956 Miller ................................ 137/510

2,790,454 4/1957 Benzel ................................ 137/510

*Primary Examiner*—Edward M. Coven

*Assistant Examiner*—J. P. Lacyk

*Attorney, Agent, or Firm*—McGlew and Tuttle

[57] ABSTRACT

A lung-controlled diaphram valve for respirator masks includes a device for creating a positive pressure in the interior of the mask, the device includes a tilting lever which by spring elements can be moved from a dead center position into a first pressure position exerting a force on the diaphragm or into a second disconnecting pressure position lifting the diaphragm off the valve lever. During the entire respiration cycle a positive pressure continuously prevails in the interior of the mask, it being prevented also that, by the movement of the diaphragm, the tilting lever can be brought into a stable disconnecting position. In addition, after use, an intentional disconnecting of the positive pressure is possible. To this end it is provided that the diaphragm has a tappet for the tilting lever which protrudes into the outer chamber of the valve. The residual stroke (a) of the tappet, when the inlet valve is closed is smaller than the residual tilting path (b) of the tilting lever between its pressure position and its dead center position. The outer chamber housing has an actual element by which the tilting lever is moveable against an end piece of the tappet.

6 Claims, 2 Drawing Figures

LUNG-CONTROLLED DIAPHRAGM VALVE

FIELD AND BACKGROUND OF THE INVENTION

This invention relates in general to respiration devices and in particular to a new and useful lung-controlled diaphragm valve for respirator masks.

The invention relates particularly to a lung-controlled diaphragm valve for respirator masks with a device for creating a positive pressure in the interior of the mask, which device contains a tilting lever hinged to the outer chamber housing and connected at its one end to move with the diaphragm, which tilting lever is so clamped by spring elements that it can be moved in a tilting joint from a dead-center position into a first pressure position exerting a force on the diaphragm and into a second disconnecting position lifting the diaphragm off the valve lever.

A similar lung-controlled diaphragm valve has become known from U.S. Pat. No. 2,780,454. In the known diaphragm valve, a tilting lever is moveable fastened by its one end to the diaphragm and by its other end it is hinged to the outer chamber housing via a block. At the same joint block helical springs are fastened which at the level of the tilting lever end connected with the diaphragm are connected therewith through pegs. The lever arms of the helical springs and tilting lever are chosen so that as the tilting lever is moved out of the dead-center position by the pull of the helical springs, a continuous pressure, increasing with the deflection, is exerted on the diaphragm. In a closing position of the inhalation valves, the tilting lever is in the dead center position or preferably slightly beyond it. The helical springs then steer it up to an abutment into a disconnecting position, in which the diaphragm is slightly lifted off the inhalation valve and the valve is closed in a stable manner. Upon inhalation, the mask wearer must first create a vacuum which moves the tilting lever over the dead center position, and opens the inhalation valve. In the further course of the inhalation, by the deflection of the tilting lever and by the pressure on the diaphragm additionally exerted thereby, the inhalation valve is opened wider than would be necessary for supplying the mask wearer with respiratory gas. Thereby a positive pressure is created in the interior of the mask which increases with the intensity of the inhalation and returns to the initial value when inhalation ends. The diaphragm valve is again in the disconnecting position, in which it remains during exhalation.

With the known lung-controlled diaphragm valve, therefore, a periodical alternation between positive pressure and vacuum takes place in the interior of the mask. While this may be desirable in medical applications for breathing assistance, such operation is unsuitable for gas mask breathing equipments, because it periodically abolishes the protective effect of the positive pressure against invasion of pollutants. Also it does not facilitate exhalation, because the exhalation valve must be adapted to the highest operating pressure.

SUMMARY OF THE INVENTION

The present invention provides a lung-controlled diaphragm valve in which a positive pressure prevails continuously in the interior of the mask during the entire respiration cycle, it being prevented that through the movement of the diaphragm the tilting lever is brought into a stable disconnecting position, and after use an intentional disconnection of the positive pressure is possible.

The diaphragm comprises a tappet for the tilting lever which protrudes into the outer chamber such as a residual stroke which is smaller when the inlet valve is closed than the residual tilt path of the tilting lever between its pressure position and its dead center position, and the outer chamber housing comprises an actuating element by which the tilting lever is moveable to an end piece of the tappet.

The advantage of the invention resides mainly in that for the diaphragm a stroke limitation is provided which prevents the diaphragm from bringing the tilting lever into the region of the dead center upon interruption of the removal of gas or upon exhalation. The tilting lever thus always remains in the pressure position during use. Hence the positive pressure in the interior of the mask is maintained during respiration also with the inlet valve closed, and the equipment wearer need not create a vacuum at the beginning of the inhalation phase to open the inlet valve. At higher internal pressure the diaphragm can indeed be lifted off the valve lever, but the tilting lever is thereby not moved into its stable disconnecting position, but rather it continues to exert its pressure force on the diaphragm, so that even the force required for the desired static pressure in the interior of the mask is exerted on the diaphragm.

If, with the respiratory gas supply connected, the respirator mask is to be taken off or the lung-controlled diaphragm valve is to be removed from it, one can bring the diaphragm valve into a stable disconnecting position with the actuating element. By actuation, the tilting lever is moved out of the pressure position beyond its dead center position into its disconnecting position, so that it engages at the end piece of the tappet and lifts the tappet by the distance of the residual stroke against the inner wall of the outer chamber housing which acts as an abutment. By the same amount the diaphragm is detached from the valve lever. Thus a secure disconnection of the diaphragm valve is ensured and it is then possible to separate the mask from the face or respectively from the diaphragm valve without loss of respiratory gas. Also it is possible to store or to transport the separate diaphragm valve with the inlet valve securely closed, without compressive forces acting on the diaphragm. To move the tilting lever from its disconnecting position into the pressure position it suffices, with the gas mask breathing equipment put on, to create a vacuum once at the beginning of the first inhalation phase, so that via the tappet the diaphragm moves the tilting lever out of its disconnecting position into the stable pressure position.

An especially favorable design for the actuation of the tilting lever into the disconnecting position is achieved by the fact that the tilting lever is divided as a two-armed lever into a pressure arm and a disconnecting arm and the actuating element engages at the disconnecting arm. Thereby a tilting of the tilting lever into its disconnecting position is brought about by the user of the diaphragm valve in a simple manner by pushing the actuating element down.

An expedient and especially rational design of the tilting joint results in that it is held by a strap anchored in the outer chamber housing.

In an appropriate variant the actuating element is a button type, elastically deformable thickening of a covering surrounding the outer chamber housing in which the thickening is recessed. Thus the guiding and resetting of the actuating element occur simply by the inherent elasticity, while at the same time the covering prevents any intrusion of dirt and any jamming produced thereby.

A favorable feature of the tappet is that it is designed as a pin, the shank of which is embraced by the tilting lever as by a fork, and the end piece of which comprises a ram. With the inlet valve closed and with the tilting lever resting on the diaphragm, this ram is spaced from the inner wall of the outer chamber housing. Upon actuation of the tilting lever into the disconnecting position, its forked end piece is pressed against the ram around the shank and pulls the ram in the direction of the inner wall of the outer chamber housing up to the abutment. The inlet valve is then relieved. When the device is taken into operation, the ram again entrains the tilting lever into the pressure position.

An especially simple construction of the spring elements can be realized by designing them as helical springs which are arranged on either side of the tilting lever lying in one plane. Preferrably the tilting lever is widened at its forked end to the extent that this end covers the free spacing between the spiral springs. It is achieved thereby that in passing through the dead center of the tilting lever from the pressure position into the disconnecting position as well as vice versa the helical springs constitute a locking engagement. Thus an additional protection of the respective stable end positions of the tilting lever is obtained and it is prevented that for example due to external vibrations the tilting lever is unintentionally moved out of its disconnecting position into the pressure position.

Accordingly, there is an object of the invention to broaden the lung-controlled diaphragm valve which includes a respirator gas inlet valve which is regulated by the valve lever which bears against a diaphragm and into an improved arrangement in which a tilting lever pivotally mounted in the valve housing over the diaphragm gauges against the tappet carried by the diaphragm and is biased by a pair of springs so that it may move into a pressure position exerting force on the diaphragm which acts on the valve control lever to maintain the respirator under positive pressure conditions during respiration which can be moved to a second stable disconnect position by actuating an actuating element carried on the valve housing.

A further object of the invention is to revise a valve for uprighting respirators which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
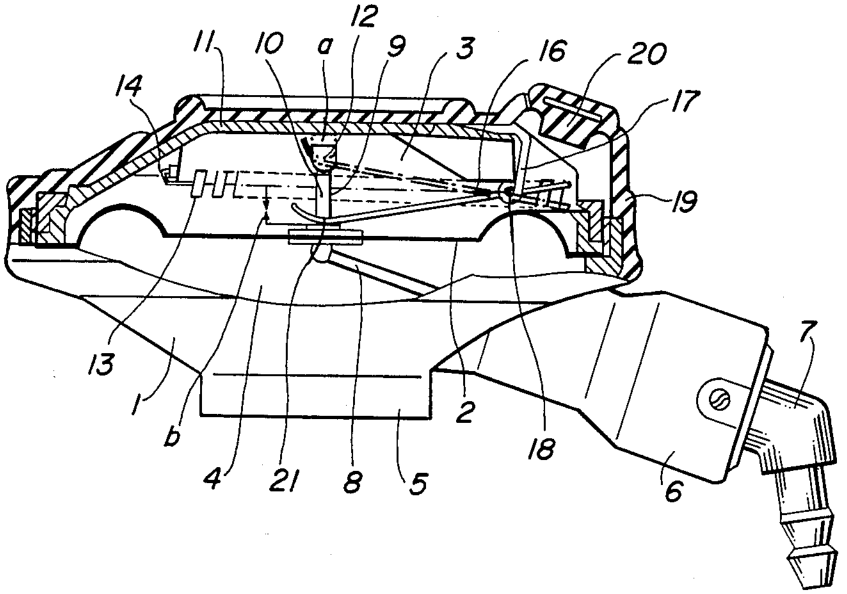
FIG. 1 is a partial sectional and side elevational view of a diaphragm valve constructed in accordance with the invention.

Referring to the drawings in particular the invention embodied therein comprises a lung-controlled diaphragm valve which has a valve housing 1, with a valve diaphragm 2 therein, dividing the interior of the housing into a valve chamber 4 having a connection fitting 5 and a connection 7 for a respiratory gas which is controlled by a valve actuating lever 8 of the valve which is in the inlet 6 which responds to the movement of the diaphragm 2.

The diaphragm valve illustrated in FIG. 1 comprises the valve housing 1, which is divided by the diaphragm 2 into an outer chamber 3 communicating with the atmosphere and the valve chamber 4 carrying the respiratory gas. The valve chamber 4 has the connecting nipple or fitting 5, to which can be coupled a respiratory mask (not shown). The valve chamber 4 is connected to the inlet valve 6, to which a connecting nipple 7 for the fresh gas is connected. Starting at the inlet valve 6, the valve lever 8 protrudes into the valve chamber 4 and touches the diaphragm 2 at a central point. At its center the diaphragm 2 has a tappet 9 formed as a pin, the shank 10 of which has, at its side toward the inner wall of the outer chamber housing 11, a ram 12. Across the outer chamber 3 two helical springs 13 are tensioned, whose ends are anchored at the attachment piece 14 of the outer chamber housing 11 and at the holding pieces 15 of a tilting lever 16. A strap 17 recessed in the outer chamber housing 11 holds the tilting lever 16 at its tilting joints 18. The tilting joints 18 are arranged near the holding pieces 15 of the tilting lever 16. Around the outer chamber housing 11 a covering 19 is applied which, in the vicinity of strap 17, has a button-like thickening 20 forming an actuating element protruding into an opening provided in the outer chamber housing 11.

The diaphragm valve is shown in FIG. 1 in the state in which the inlet valve 6 is closed and diaphragm 2 rests on the valve lever 8. The tilting lever 16 applies by its pressure arm 21 on the diaphragm under spring pressure, so that ram 12 is held at a residual stroke distance a from the inside of the outer chamber housing 11, a being the residual stroke. The bearing point of tilting lever 16 on the membrane 2 is spaced from the dead center of tilting lever 16, shown in dash-dot lines, by a residual tilting distance b marked as a double arrow, b being the residual tilting path. In the illustrated example the dead center of the tilting lever 16 is determined by the plane in which lie the center lines of the helical spring 13 and of the tilting gear joint 18. By depression of the button 20 onto the disconnecting arm 24 limited by the tilting joint 18 and the holding pieces 15, the pressure arm 21 of tilting lever 16 is moved against the ram 12 of tappet 9, lifting it by the residual stroke a up against the inner wall of the outer chamber housing 11. In this position (shown in phantom line in FIG. 1) the tilting lever 16 is in its stable disconnecting position, in which the diaphgragm 2 is removed from the valve lever 8 by the same distance a (having been lifted off the valve lever 8 when tappet 9 was lifted by its ram 12).

Figure 2:
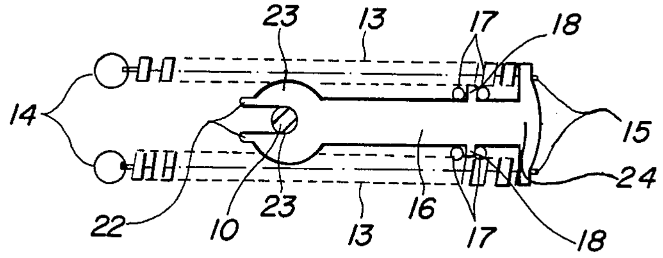
FIG. 2 is a top plan view of the tilting lever shown in FIG. 1.

The top view shown in FIG. 2 onto the tilting lever 16 shows the clamped position of the two helical springs 13. The tilting lever 16 embraces the shank 10 of tappet 9 like a fork, the fork end 22 having widened portions 23 which cover the clear distance of the helical springs 13 from each other.

When passing through the dead center of the tilting lever, the helical springs 13 must be pushed apart by a small amount as widened portions 23 pass, so that the helical spring 13 also act as catches.

While specific embodiments of the invention have been shown and described in detail to illustrate the application of the principles of the invention, it will be understood that the invention may be embodied otherwise without departing from such principles.

What is claimed is:

1. In a lung-controlled diaphragm valve having a valve housing defining a space with a valve diaphragm connected to said housing and extending across said space to divide space into an outer chamber and an inner chamber, the improvement comprising a tappet fixed to said diaphragm and extending into said outer chamber, said tappet having a ram which is spaced from said diaphragm, an inlet valve connected to said housing and communicating with said inner chamber for supplying breathing gas to said inner chamber, a valve lever connected to said inlet valve and engagable by said diaphragm to open said inlet valve, a connecting fitting connected to said housing and communicating with said inner chamber for connection to a respiratory mask for a user, a tilting lever pivotally mounted to said housing in said outer chamber, said tilting lever having a first arm portion engagable with said diaphragm and with said ram, and a second arm portion spaced from said first arm portion, an outer chamber housing enaged over said valve housing and including an actuating element moveable into said outer chamber and against said second arm portion of said tilting lever to move said first arm portion away from said diaphragm and toward enagement with said ram, and at least one spring connected between said housing in outer chamber and said tilting lever for biasing said first arm portion into engagement with said diaphragm when said tilting lever is in a pressure position engaged with said diaphragm, and for biasing said first arm portion away from said diaphragm and into engagement with said ram when said tilting arm is in a disconnecting position, said ram of said tappet being spaced from an inner surface of said housing by a residual stroke distance when said tilting lever is in its pressure position with said valve lever closing said inlet valve, said tilting lever having a dead center position between its pressure position and its disconnecting position, under the influence of said spring, the distance between said pressure position and said dead center position for said first arm portion comprising a residual tilting distance, said residual tilting distance being greater than said residual stroke distance, said first arm portion of said tilting lever being moveable from said pressure position up to a position of engagement with said ram without moving said tappet, and said tilting lever being moveable into its disconnecting position with said first arm portion being engaged with said ram and pushing said ram under the influence of said spring into engagement with the inner surface of said housing in said outer chamber.

2. In a lung-controlled diaphragm valve according to claim 1 wherein said tilting lever comprises a two arm lever including said first arm portion and said second arm portion, said actuating element engaging said second arm portion, said second arm portion comprising a disconnecting arm and said first arm portion comprising a pressure arm.

3. In a lung-controlled diaphragm valve according to claim 1, including a strap carried by said valve housing extending into said outer chamber defining a pivot joint for said tilting lever.

4. In a lung-controlled diaphragm valve according to claim 2 including a strap connected to said housing and extending into said outer chamber, said tilting lever being pivotally mounted to said strap, said spring being connected between said second arm portion at a location spaced from said strap and said housing, said spring having a center line lying in a plane which contains said dead center position for said tilting lever, said tappet comprising a shank extending away from said diaphragm, said first arm portion of said tilting lever having a forked end engaged around said shank, said forked end having at least one widened portion engagable against and past said spring when said tilting lever moves from its pressure position to its disconnecting position.

5. In a lung-controlled diaphragm according to claim 4 including a second spring having a center line lying in said plane and being connected between said second arm portion and said housing in said outer chamber, said forked end of said first arm portion having a second widened portion opposite from said first mentioned widened portion and enagable with, against and past said second spring when said tilting lever moves from its pressure position to its disconnecting position.

6. In a lung-controlled diaphragm valve according to claim 2 including a strap connected to said housing and extending into said outer chamber, said tilting lever being pivotally connected at a joint to said strap, said first arm portion being on one side of said joint and said second arm portion being on an opposite side of said joint.

* * * * *